(12) United States Patent
Chiarin

(10) Patent No.: US 9,962,117 B2
(45) Date of Patent: May 8, 2018

(54) NEEDLE SUPPORT ASSEMBLY FOR A VENOUS BLOOD COLLECTION DEVICE WITH EVACUATED VIAL

(71) Applicant: VACUTEST KIMA S.r.l., Arzergrande (IT)

(72) Inventor: Renzo Chiarin, Arzergrande (IT)

(73) Assignee: VACUTEST KIMA S.R.L., Arzergrande, Padua (IT)

( * ) Notice: Subject to any disclaimer, the term of this patent is extended or adjusted under 35 U.S.C. 154(b) by 276 days.

(21) Appl. No.: 14/439,191

(22) PCT Filed: Oct. 31, 2012

(86) PCT No.: PCT/IT2012/000335
§ 371 (c)(1),
(2) Date: Apr. 28, 2015

(87) PCT Pub. No.: WO2014/068603
PCT Pub. Date: May 8, 2014

(65) Prior Publication Data
US 2015/0257694 A1    Sep. 17, 2015

(51) Int. Cl.
*A61B 5/00*    (2006.01)
*B65D 81/00*    (2006.01)
(Continued)

(52) U.S. Cl.
CPC ........ *A61B 5/150732* (2013.01); *A61B 5/153* (2013.01); *A61B 5/15003* (2013.01);
(Continued)

(58) Field of Classification Search
CPC .......... A61B 5/150732; A61B 5/15003; A61B 5/153; A61B 5/1535; A61B 5/1545;
(Continued)

(56) References Cited

U.S. PATENT DOCUMENTS 4,340,068 A * 7/1982 Kaufman ........... A61B 5/15003
                                                        600/579
4,767,408 A   8/1988 McFarlane
(Continued)

FOREIGN PATENT DOCUMENTS

| CN | 2857819 Y | 1/2007 |
| CN | 101026999 A | 8/2007 |
| WO | WO 2011/047413 A1 | 4/2011 |

OTHER PUBLICATIONS

International Search Report for PCT/IT2012/000335 dated Jul. 9, 2013.

*Primary Examiner* — Devin Henson
(74) *Attorney, Agent, or Firm* — Arent Fox LLP

(57) ABSTRACT

Needle support assembly for a venous blood collection device with evacuated vial, comprising a support body having a coupling seat for a vein needle and coupling seat for a vial needle. The support body is provided with an inner chamber having an entrance and an exit. The support body is made at least partially in transparent or semi-transparent material to permit the visualization of the blood flow. The inner chamber has a mean cross-section greater than the cross-sections of both the coupling seats and is divided into compartments communicating with each other which define one or more channels for the blood flow from the entrance to the exit. Each channel defines a path for the blood which moves away from the entrance to the exit. Each channel defines a path for the blood which moves away from the straight line connecting the entrance and the exit and has a smaller cross-section than the mean cross-section of the inner chamber.

19 Claims, 6 Drawing Sheets

(51) Int. Cl.
*A61B 5/15* (2006.01)
*A61B 5/154* (2006.01)
*A61M 5/32* (2006.01)
*A61M 5/34* (2006.01)
*A61M 25/06* (2006.01)
*A61B 5/153* (2006.01)
*A61M 5/158* (2006.01)

(52) U.S. Cl.
CPC ...... *A61B 5/1545* (2013.01); *A61B 5/150221* (2013.01); *A61B 5/150251* (2013.01); *A61B 5/150343* (2013.01); *A61B 5/150389* (2013.01); *A61B 5/150473* (2013.01); *A61B 5/150572* (2013.01); *A61M 5/3293* (2013.01); *A61M 5/34* (2013.01); *A61M 5/347* (2013.01); *A61B 5/1422* (2013.01); *A61B 5/1535* (2013.01); *A61M 25/0693* (2013.01); *A61M 2005/1588* (2013.01); *F04C 2270/0421* (2013.01); *Y10S 604/90* (2013.01)

(58) Field of Classification Search
CPC ........... A61B 5/1422; A61B 5/150251; A61M 25/0693; A61M 2005/2588; Y10S 604/90
See application file for complete search history.

(56) References Cited

U.S. PATENT DOCUMENTS

| | | |
|---|---|---|
| 5,820,596 A | 10/1998 | Rosen et al. |
| 2003/0105414 A1 | 6/2003 | Leong |
| 2005/0027233 A1 | 2/2005 | Flaherty |
| 2009/0227953 A1 | 9/2009 | Tan et al. |
| 2010/0204553 A1 | 8/2010 | Sonderegger |
| 2011/0178427 A1 | 7/2011 | Tan et al. |
| 2012/0232424 A1 | 9/2012 | Rodd et al. |

\* cited by examiner

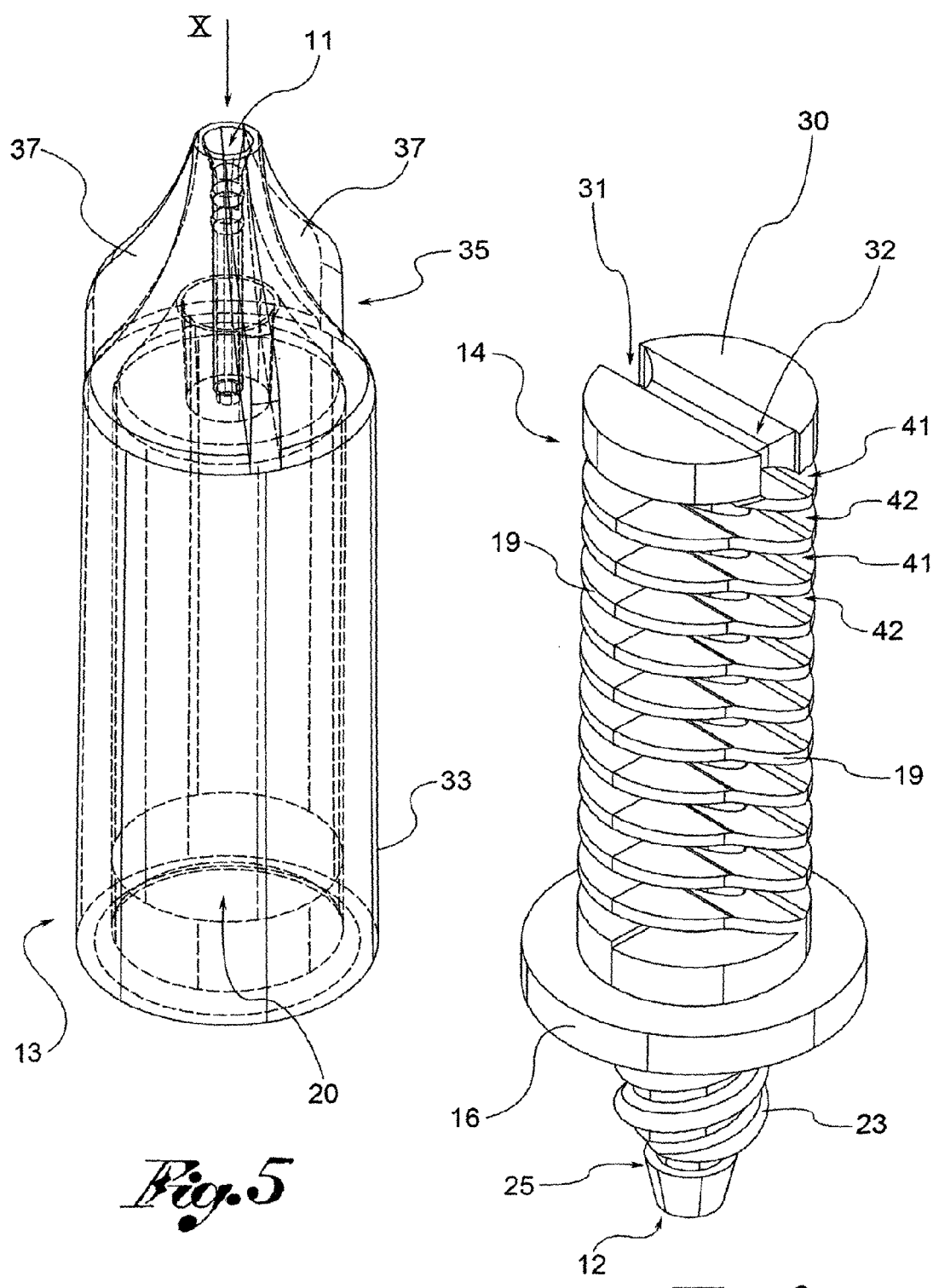

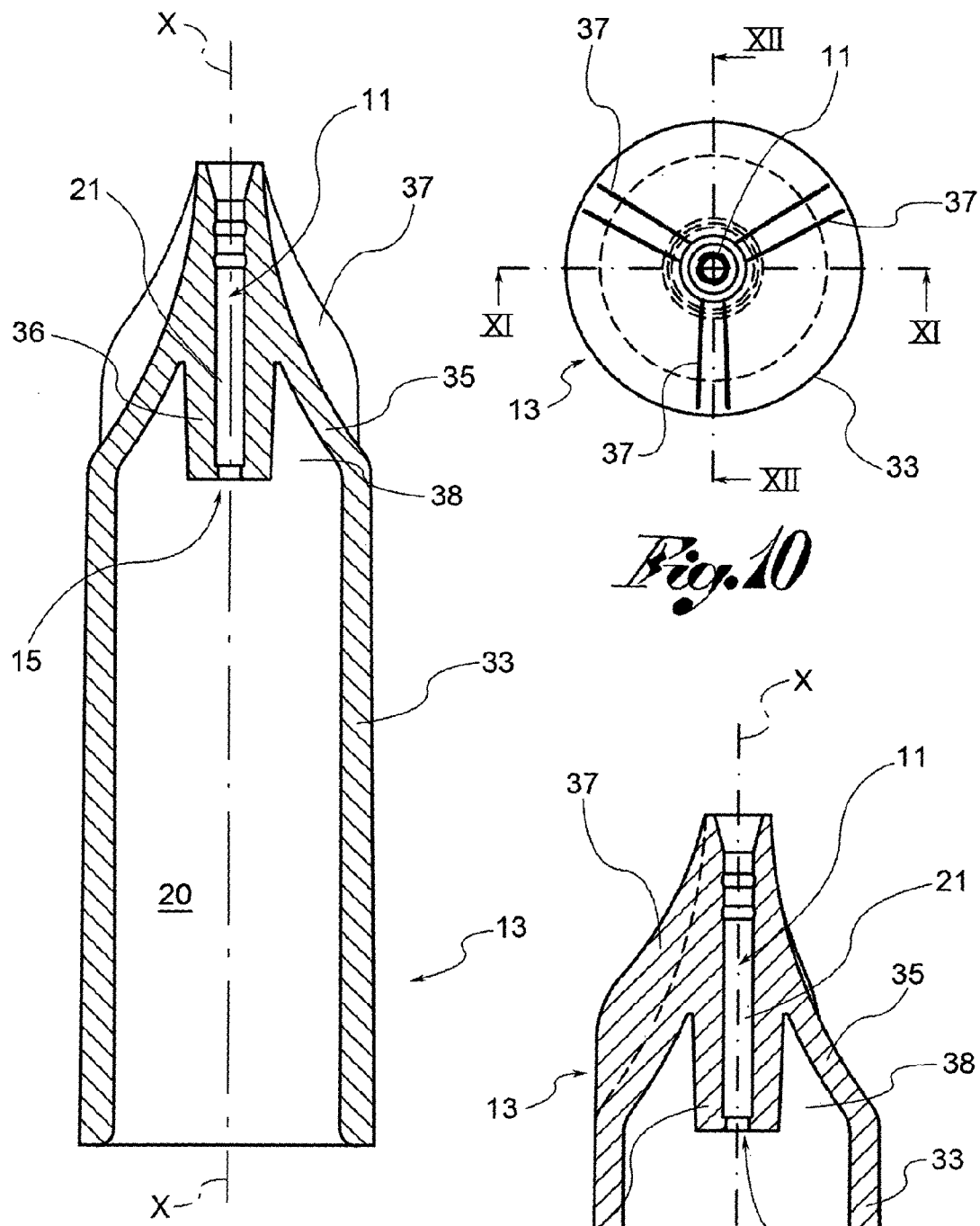

NEEDLE SUPPORT ASSEMBLY FOR A VENOUS BLOOD COLLECTION DEVICE WITH EVACUATED VIAL

CROSS-REFERENCE TO RELATED APPLICATIONS

This application is a National Stage entry of International Application No. PCT/IT2012/000335, filed Oct. 31, 2012, the entire contents of which are incorporated herein by reference in their entirety.

FIELD OF APPLICATION

The present invention relates to a needle support assembly for a venous blood collection device with evacuated vial.

STATE OF THE ART

As is known, in venous blood collection the entrance of the needle in the vein is an operation which is not always easy. It often happens that to be sure of being in a vein the operator may have to investigate the point of collection on the patient's body quite thoroughly and, despite this, may even have to repeat the operation, in that the vein has not been intercepted at the first attempt.

In blood collection performed using a syringe, the problem of entering the vein is actually of little relevance. Entrance in the vein is, moreover, easily verifiable by the operator in that the needle communicates directly with the blood collection chamber. Consequently, in the case of failure to enter the vein, by operating the plunger of the syringe the absence or scarcity of blood flow into the collection chamber is immediately verified.

The problem of entering the vein is, on the contrary, relevant in the case of collection performed using collection systems with predetermined evacuated vials.

As is known, these systems comprise a vial holder body (in the jargon "holder"), composed of a socket having on the bottom a threaded aperture, and a needle support assembly element, consisting of a hub which at a first end holds a first needle (destined to enter the vein, hereinafter called vein needle), and at a second end a second needle (destined to perforate the seal of an evacuated vial, hereinafter vial needle). The two needles are inserted inside a channel inside the hub which connects them fluidically. The two needles may even be made in a single body with each other. The needle support assembly is associated to the holder at the second end, so that the vial needle (covered by a rubber shut-off valve) projects inside the socket. The predetermined evacuated vials are provided with a performable sealing plug. Once the vial is inserted n the holder, the vial needle penetrates inside said vial through the plug thereby placing the vein needle in communication with the evacuated vial. The vial is inserted in the holder after inserting the needle in the vein. If the vein, is entered correctly, the vacuum of the vial permits the flow of blood into the vial; if the vein has not been entered, the blood cannot be aspirated and the operation has to be repeated. In the latter case however, the vial must be replaced in that it has lost some or all of its aspirating capacity.

The problem has been tackled for some time by proposing collection systems provided with means of visualising the blood flow in the needle before inserting the vial in the holder. A viewing window is generally created as close as possible to the perforation tip.

One example of such systems is described in the patent application US2009/0227953. The hub of the needle support assembly element is composed of a cone in transparent or semi-transparent plastic material, inside which two chambers are defined. A first chamber is substantially defined by the channel inside the hub, while the second chamber extends coaxially to the first. In the case of two separate needles, the vein needle and the vial needle are inserted inside the inner channel so that their two ends are not in contact, so as to create a blood flow area external to the needles. In the case of a single needle, an aperture is made in the needle—at the inner channel of the hub—to allow the blood to flow out into the inner channel. Thanks to the transparency of the hub such external flow area defines a viewing window. In both cases, the second chamber is a closed chamber, which communicates fluidically only with the first chamber (the inner channel). Thanks to venous pressure the blood flows out of the needle inside the channel compressing the air contained in such second chamber which is at atmospheric pressure.

The collection devices with visualisation of the blood flow present on the market are structured so that only a small amount of blood enters the visualisation area. This is an advantage in that it minimises the blood lost in the visualisation, but also has some drawbacks.

A first drawback is related to the fact that the reduced dimensions of the window make visualisation and control operations by the operator difficult.

A second drawback is related to the fact that-given its reduced size, and position near the vein needle-in some cases the visualisation window may fill even when the vein has not been entered correctly. The blood present in tissues may in fact have sufficient pressure to fill the viewing window and thereby give the operator an incorrect signal.

PRESENTATION OF THE INVENTION

Consequently, the purpose of the present invention is to eliminate or at least reduce the drawbacks of the prior art mentioned above, by making available a needle support assembly for a venous blood collection device with evacuated vial, which makes it possible to correctly verify the entrance of the needle in the vein.

A further purpose of the present invention is to make available a needle support assembly for a venous blood collection device with evacuated vial, which is operatively reliable, without risk of accidental effusion and in total safety.

A further purpose of the present invention is to make available a needle support assembly for a venous blood collection device with evacuated vial, which is economically simple to produce.

BRIEF DESCRIPTION OF THE DRAWINGS

The technical characteristics of the invention, according to the aforesaid purposes, can be seen clearly from the contents of the following claims and the advantages of the same will be more clearly comprehensible from the detailed description below, made with reference to the attached drawings, showing one or more embodiments by way of non-limiting examples, wherein:

FIG. 5 shows a first component of the needle support assembly in FIG. 1, consisting of an outer casing with coupling portion of the vein needle;

FIG. 6 shows a second component of the needle support assembly in FIG. 1, consisting of a body insertable inside the casing in FIG. 5 and provided with a portion coupling to the vial needle and connecting to the holder;

FIG. 10 shows an axial view of the outer casing in FIG. 5 according to the arrow X shown therein;

FIG. 11 shows a cross-section view of the casing in FIG. 5 according to the section plane XI-XI indicated in FIG. 10; and FIG. 12 shows a cross-section view of a detail of the casing in FIG. 5 according to the section plane XII-XII indicated in FIG. 12.

DETAILED DESCRIPTION

Figures 1, 2:
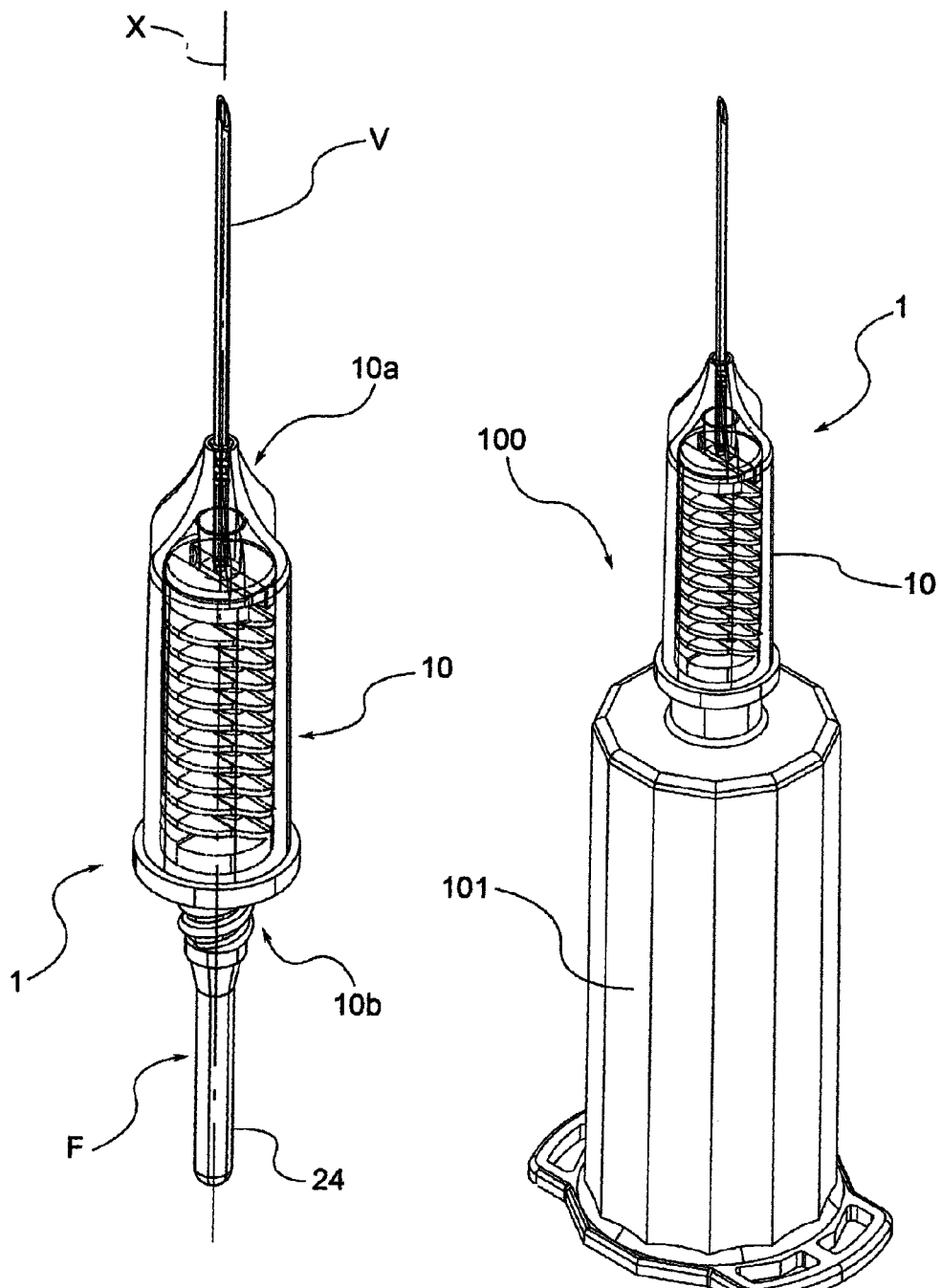
FIG. 1 shows a schematic perspective view of a needle holder assembly according to a preferred embodiment of the invention, shown with the vein needle and the vial needle.
FIG. 2 shows a perspective view of a blood collection device with the needle support assembly in FIG. 1 coupled to an holder.

With reference to the appended drawings, reference numeral 1 globally denotes a needle support assembly for a venous blood collection device with evacuated vial according to the invention and reference numeral 100 a venous blood collection device with evacuated vial according to the invention.

According to a general embodiment of the invention, the needle support assembly 1 comprises a support body 10 which extends along a longitudinal axis X between a first end 10a and a second end 10b. At such first 10a and second 10b ends a coupling seat 11 for a vein needle V and a coupling seat 12 for a vial needle F are respectively made.

The support body 10 is provided with an inner chamber 20 having an entrance 21 and an exit 22, which communicate fluidically with the vein needle coupling seat 11 and with the vial needle coupling seat 12 respectively to permit the blood flow.

The support body 10 is made at least partially in transparent or semi-transparent material to permit the visualisation of such blood flow.

In relation to a section plane orthogonal to the longitudinal axis X the inner chamber 20 has a mean cross-section greater than the cross-sections of both the coupling seats 21, 22.

The inner chamber 20, is divided into compartments communicating with each other which define one or more channels 41, 42 for the blood flow from the entrance 21 to the exit 22. Each channel 41, 42 defines a path for the blood which moves away from the straight line connecting the entrance 11 and the exit 12 and has a smaller cross-section than the mean cross-section of the inner chamber 20.

Operatively, at the moment of entering the vein the aforesaid channels 41 and 42 will be filled only partially by the blood, while with the insertion of an evacuated vial they will be entirely filled by the blood flow.

The dimensions of the inner chamber 20 (having as already said a mean cross-section greater than the cross-sections, of both the coupling seats 21, 22) ensure that inside the needle support assembly—before connection to an evacuated vial—a volume of air is present, compressible by the blood flow, greater than that strictly needed for an obstruction free blood flow from the vein needle to the vial needle. The availability of a greater volume of compressible air permits the entrance of a greater quantity of blood in the needle support assembly in the case of the correct entrance of the needle in the vein.

Operatively, before the insertion of the vein needle V in the vein the air contained in the inner chamber 20 is at atmospheric pressure. In the case of the correct entrance of the needle in the vein the blood flows inside the chamber thanks to the overpressure given by the venous blood pressure. The air then progressively compresses until it reaches an equilibrium with the venous blood. The compression of the air is possible in that the vial needle is not open on the outside, but is closed by a (perforable) shut-off valve 24, as will be explained further on in the description.

The presence of the aforesaid one or more channels 41, 42 having a mean flow cross-section smaller than the mean transversal cross-section of the inner chamber makes it possible to have a distribution of the blood entering the needle support assembly over a volume having a more accentuated linear extension. This makes a more evident clearer visualisation of the blood flow in the needle support assembly possible and therefore easier recognition of the situation of the correct entrance of the needle in the vein.

Thanks to the fact that the needle support assembly 1 according to the invention permits the entrance of a greater quantity of blood, distributed over a volume with a substantially linear extension, the difference between a situation of failure to enter the vein (little blood entering) and correct entrance in the vein (a lot of blood entering) is heightened. This considerably facilitates verification by the operator.

Preferably, the mean flow cross-section of each channel 14, 42 is greater than the mean flow cross-section of the vein needle V to prevent unwanted obstruction of the blood flow and the correlated phenomena of haemolysis.

According to the preferred embodiment shown in the appended drawings, the entrance 11 and exit 12 are aligned longitudinally with each other and with the coupling seats 21 and 22. In particular, each channel 41, 42 defines a path for the blood which moves away from the longitudinal axis X.

Embodiments may be envisaged (not shown in the appended drawings) in which the entrance and exit of the inner chamber are not longitudinally aligned with each other.

Preferably, as shown in the appended drawings, the compartments of the inner chamber 20 define at least two channels 41, 42 which are connected parallel to each other next to the entrance 21 and the exit 22. The presence of two or more parallel channels reduces the response times in the visualisation of entrance in the vein, given that compared to a single channel the blood must cover a shorter path before the pressure in the chamber reaches an equilibrium with the venous blood pressure.

Embodiments may however be envisaged (not shown in the appended drawings) in which the compartments of the inner chamber 20 define a single channel for the blood flow.

Preferably, as shown in the appended drawings, the aforesaid one or more channels 41, 42 for the blood flow mainly occupy the axially outermost portion of volume of the inner chamber 20. This permits a peripheral distribution of the blood entered the needle support assembly. Such peripheral distribution, combined with the fact that the quantity of blood entering the needle support assembly is distributed over a volume with a substantially linear extension, allows a clear and more evident visualisation of the blood flow (in the case of correct entrance of the needle in the vein) compared to the traditional systems in which the blood flow takes place in an axially inner portion of the needle support assembly.

Preferably, as will be explained in more detail below the aforesaid one or more channels 41, 42 for the blood flow occupy only the axially outermost portion of volume of the inner chamber 20, while the remaining axially inner portion of the inner chamber 20 is not affected by the aforementioned channels and is therefore precluded from the blood flow. On the one hand this makes it possible to improve the visualisation of the blood flow and on the other to reduce the quantity of blood needed to visualise the correct entrance in the vein. The blood is in fact concentrated in the peripheral area more suitable for visualisation.

Advantageously, as shown in the appended drawings, the aforesaid one or more channels 41, 42 extend mainly on planes orthogonal to the longitudinal axis X. This makes it possible to arrange the paths for the blood flow so as to maximise the volume available in the inner chamber 20.

Preferably, the aforesaid one or more channels 41, 42 each have spiral-shaped extension. In particular, such channels have a spiral extension around axes parallel to the longitudinal axis X, and in particular around the longitudinal axis X. The spiral extension has in particular the advantage of reducing turbulence to a minimum in the blood collection step with a consequent lesser risk of triggering haemolysis phenomena.

According to the preferred embodiment shown in the appended drawings, the compartments which the inner chamber is divided into define two of the aforementioned channels 41,42. Such two channels 41, 42 extend in two axially superimposed spiral shaped paths, coaxial to the axis X, with a double spiral structure. More specifically, a first channel 41 extends in a clockwise turning spiral and the second channel 42 extends in an anti-clockwise turning spiral. As may be observed in the appended drawings, in particular, such two spiral shaped channels mainly occupy the axially outermost portion of volume of the inner chamber.

The extension of the channels is preferably in a spiral pattern. Embodiments may however be envisaged (not shown in the appended drawings) in which such channels have an extension which is not spiral-shaped, but which in any case moves away from the straight line connecting the entrance and the exit. For example, the paths may be substantially rectilinear, parallel to the longitudinal axis X (not coaxial), so as to be arranged in radial arrangement in relation to the longitudinal axis X.

According to the aforesaid preferred embodiment, the support body 10 comprises an outer containment casing 13, which defines the inner chamber 20, and a partitioning element 14, which is positioned inside such casing 13 to create the aforesaid one or more channels 41, 42.

Advantageously, the sheath 13 and the partitioning element 14 are two separate components, associated to each other by a shape coupling and attached in a non-detachable manner, for example by ultrasound soldering.

In particular, as shown in the appended drawings, the aforesaid casing 13 is composed of a socket body 33, provided on its bottom 35 with a first aperture 15 which defines the entrance 21 of the inner chamber 20, and at which aperture the coupling seat 11 for the vein needle V is made. The socket body 33 may be a substantially cylindrical shape.

As shown in particular in FIGS. 10, 11 and 12, the bottom 35 of the socket body 33 is the shape of a hollow cone. Inside the hollow cone a tubular tail-piece 36 extends which communicates with the outside and with the inside and defines the coupling seat of the vein needle V. At the cone bottom the socket body is provided externally with one or more tabs 37, utilisable for applying the rotation force needed to screw the threaded portion (described below) of the needle support assembly to a holder more easily.

In particular, as shown in the appended drawings, the partitioning element 14 supports at one of its ends 14a a flange 16 which abuts with the socket body 33 to close the inner chamber 20. A second aperture 17 is made on the flange 16, which aperture defines the exit 22 of the inner chamber 20 and at which the coupling seat 11 for the vial needle F is made. More specifically, a tubular tail-piece 23 extends outwards from the flange 16, which piece communicates with the outside and with the inside and defines the coupling seat of the vial needle F. Such tubular tail-piece is threaded externally and is suitable for coupling with a counter threaded portion of a holder.

More in particular, the partitioning element 14 comprises an axially elongated body 18 which extends from the flange 16 coaxially to the axis of the cylindrical socket body. A plurality of tabs 19 extend radially from such elongated body 18, which divide the inner chamber 20 into the aforesaid compartments 41, 42.

Preferably, as shown in the appended drawings, the axially elongated body substantially occupies the innermost portion of volume of the chamber 20 along the longitudinal axis X, thereby leaving the axially outermost volume of the chamber 20 free for the blood flow.

In particular, the tabs 19 are in contact with the socket body 33 of the casing 13. The channels 41, 42 are therefore delimited by such tabs 19, by the axially elongated body 18 and by the socket body 33.

Preferably, the tabs 19 have a spiral shape extension around the axially elongated body 18.

According to the preferred embodiment shown in the appended drawings, the tabs 19 are structured as two continuous coaxial spirals, axially superimposed with each other, so as to define a double spiral. In particular, one spiral runs clockwise and the other anti-clockwise. Such two spiral shaped tabs 19 define between them two separate, axially superimposed spiral-shaped channels 41, 42.

From a construction point of view, the double spiral structure of the tabs permits easier construction of the die for moulding and therefore simpler production.

According to the aforesaid preferred embodiment, the axially elongated element 18 supports—in an axially opposite position to the flange 16—a disc 30 which has a cross-section corresponding to the inner transversal cross-section of the socket body 33 and which is placed next to the bottom 35 of the socket body 33. On such disc 30 one or more separate grooves 31, 32 are made, each of which places the first entrance aperture 15 of the blood flow in communication with one of the aforesaid channels 41, 42.

Figure 3:
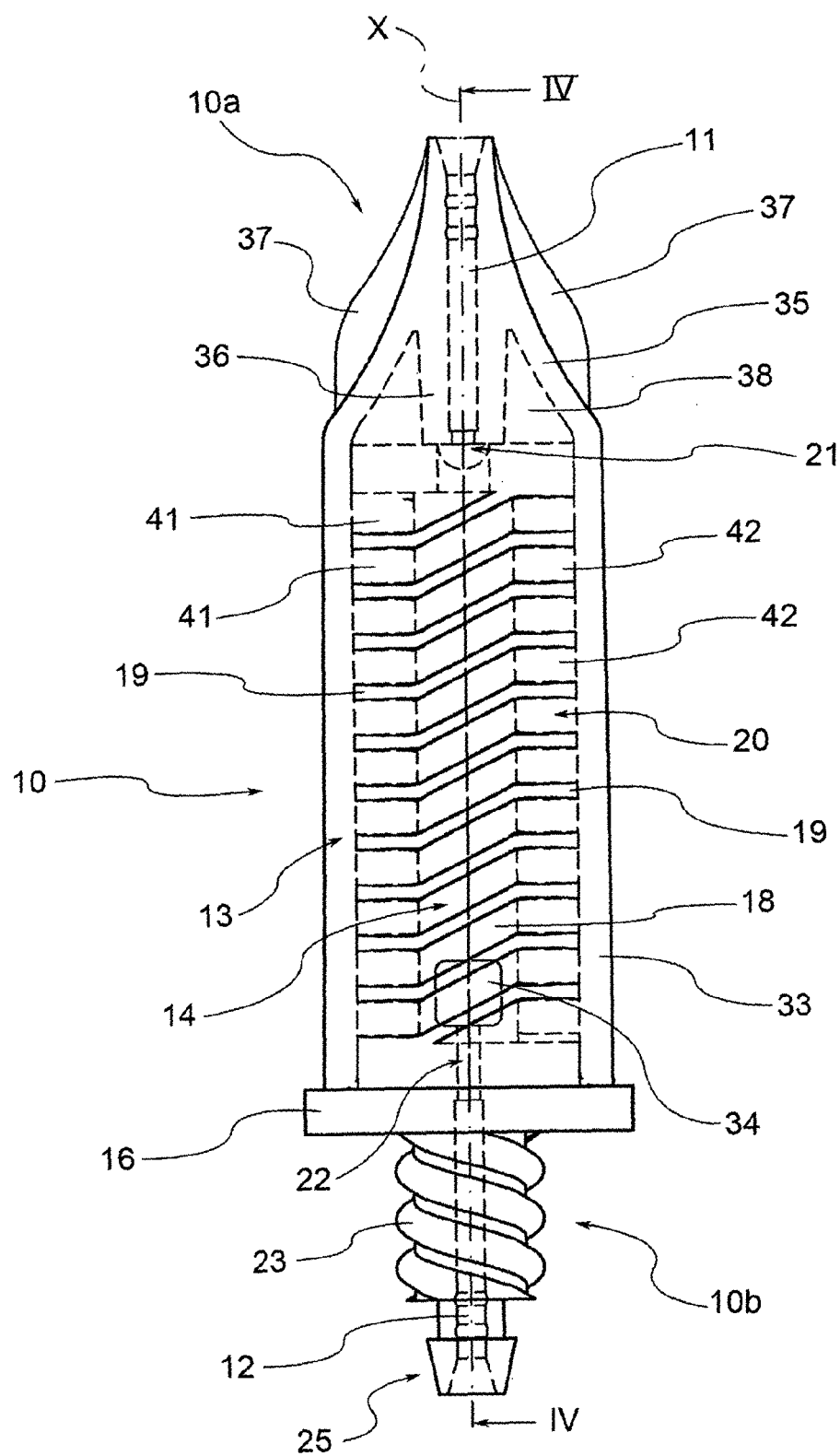
FIG. 3 shows a lateral view of the needle support assembly in FIG. 1.
Figure 4:
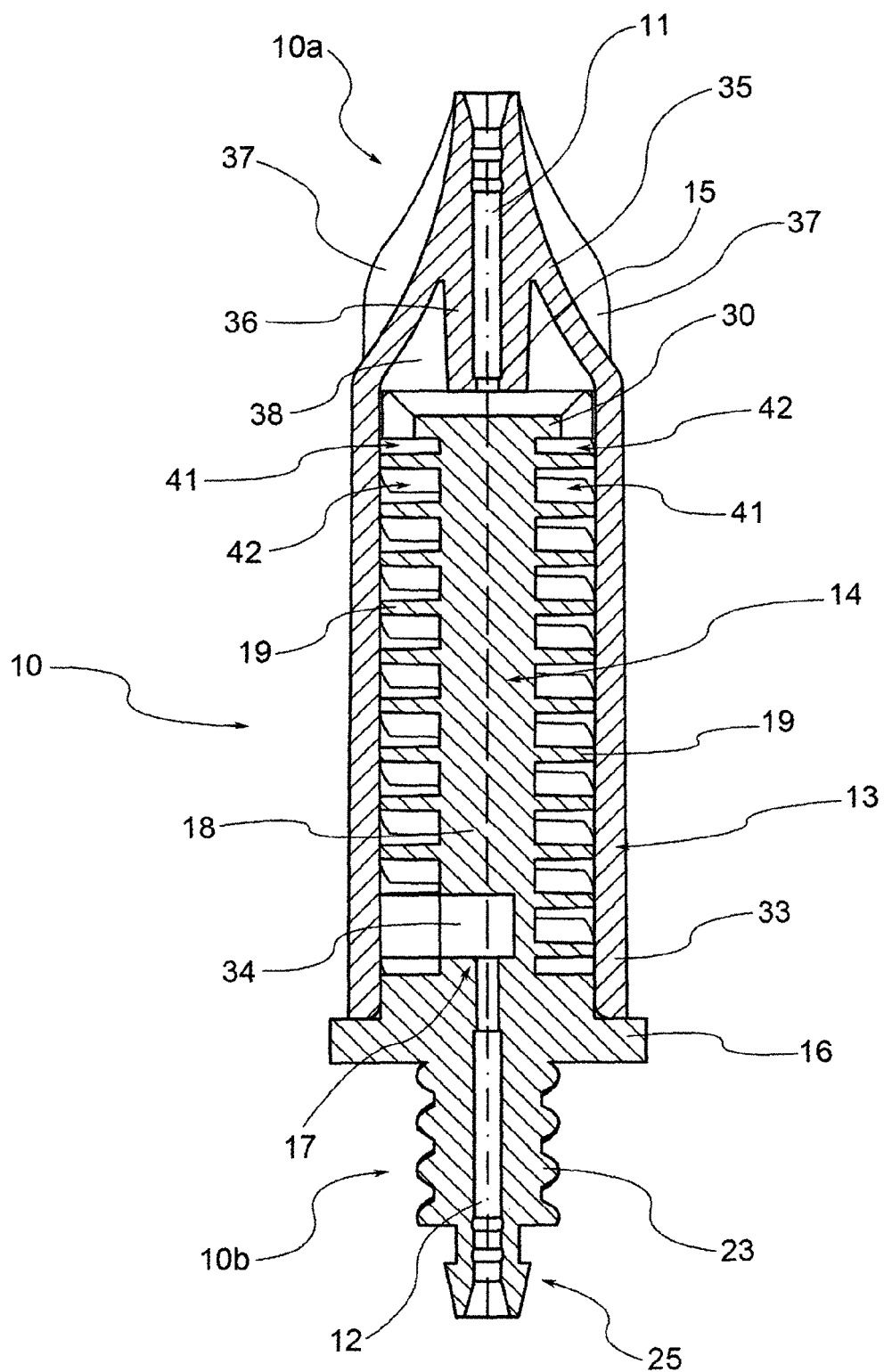
FIG. 4 shows a cross-section view of the needle support assembly in FIG. 3 according to the section plane IV-IV indicated therein.

As shown in FIGS. 3 and 4, the blood coming from the vein needle V flows through a tubular tail piece 36 inside the chamber, encounters the disc 30 and flows into the grooves 31, 32 to enter the channels 41, 42.

Preferably, between the cone-shaped bottom 35 of the socket body and the tubular tail-piece 36 (which defines the coupling seat of the vein needle) a cone-shaped cavity 38 is formed which is fluidically open on the inner chamber 20 and on the disc 30. The blood can therefore fill such cone-shaped cavity as well as flow into the channels 41, 42.

Advantageously, at an axial portion next to the flange 16 the axially elongated element 18 has an inner cavity 34 which communicates fluidically with the second exit aperture 17 of the inner chamber 20 and with the aforementioned one or more channels 41,42. In the presence of an evacuated vial fluidically connected to the vial needle F the blood coming from the aforesaid channels 41, 42 flows into such inner cavity 34, which has a preferably axial extension, to then flow into the vial needle F.

Preferably, the socket body 33 of the outer casing 13 is made in transparent or semi-transparent material at least for a first axial portion which extends from the bottom 35 of the socket body. Advantageously, the socket body is also made in transparent or semi-transparent material at the cone shaped cavity 38 so as to permit visualisation of the blood flow already in such cavity 38 even before the flow into the channels.

Preferably, the needle support assembly is structured in such a way that the aforesaid one or more channels 41, 42 have an overall volume of not less than 300 mm$^3$.

Figure 7:
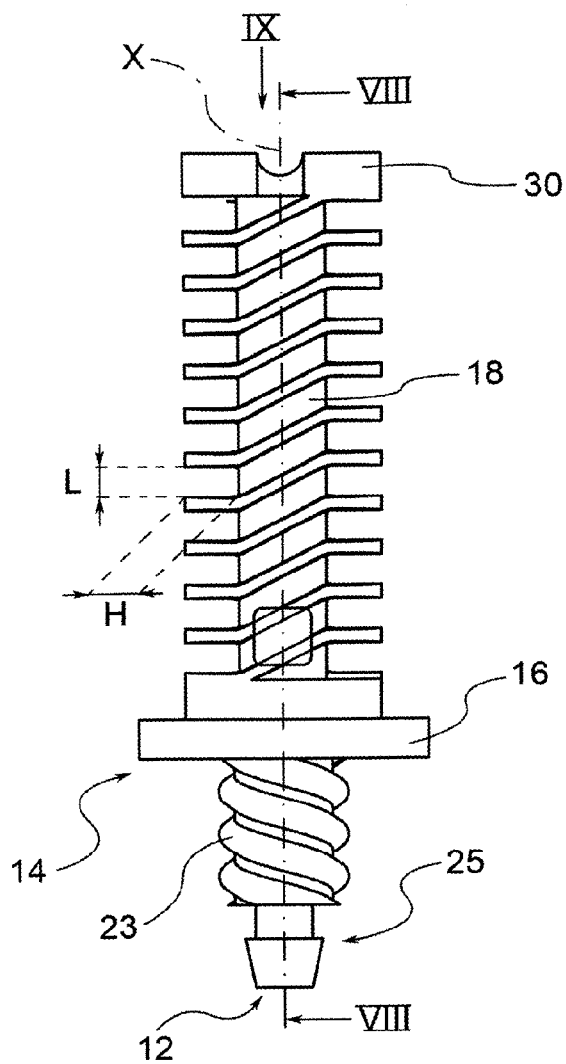
FIG. 7 shows a lateral view of the insertable body in FIG. 6.
Figure 8:
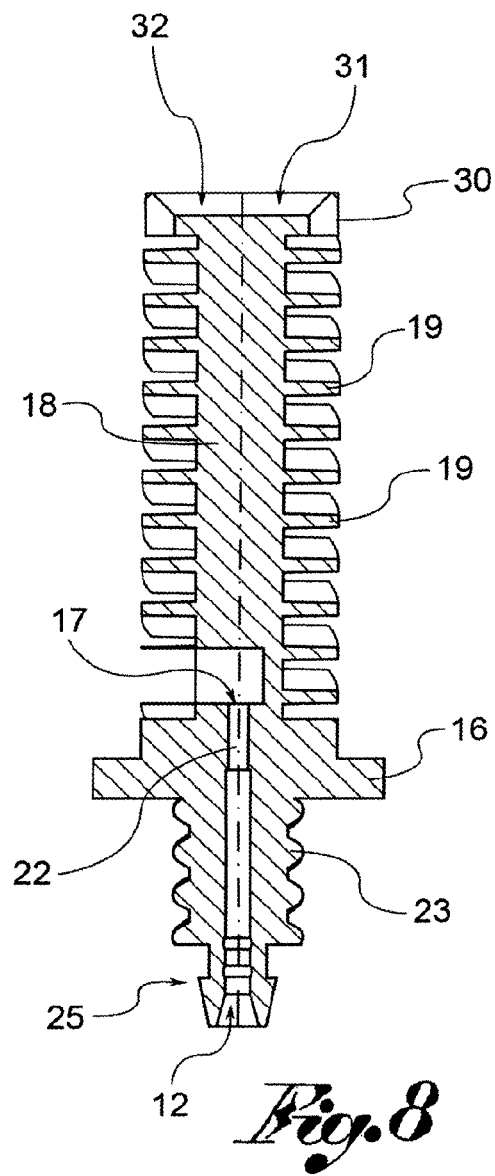
FIG. 8 shows a cross-section view of the insertable body in FIG. 7 according to the section plane VIII-VIII indicated therein.
Figure 9:
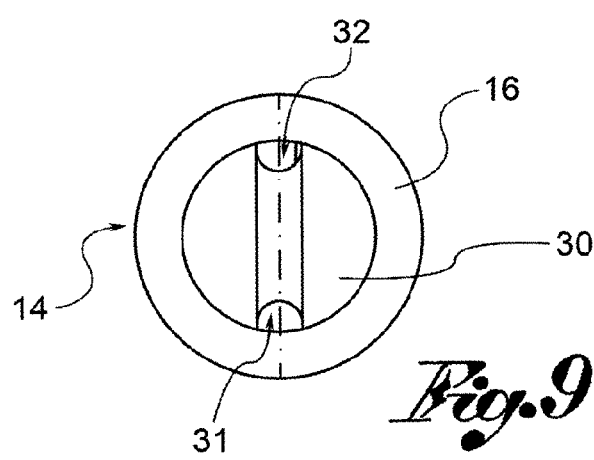
FIG. 9 shows an axial view of the insertable body in FIG. 7 according to the arrow IX shown therein.

The main dimensions of a needle support assembly according to the invention destined in particular for a vein needle classified in the sector of reference as needle 21G (total length needle 34 mm; length of needle projecting from the support 25 mm; outer diameter 0.80 mm and inner diameter 0.55 mm). The needle support assembly has the characteristics shown in the appended drawings. The inner chamber 20 has an overall volume of 769 mm$^3$, including the volume of the cone-shaped cavity 38 of 50 mm$^3$. The two spiral-shaped channels 41 and 42 each have a volume of 205 mm$^3$, for a total of 410 mm$^3$. Each channel 41, 42 has a flow cross-section of 1.99 mm$^2$ (rectangular cross-section with L=1.06 mm and H=1.88 mm, as shown in FIG. 7). Each channel has a linear extension of 102.87 mm.

From tests performed, it was possible to ascertain that in the case of correct entrance in the vein the blood fills the entire cone-shaped cavity 38 and from one to two coils of both channels 41 and 42. Visualisation is thus very clear and evident. In the case of incorrect entrance in the vein the blood does not generally fill even the entire cone-shaped cavity 38.

The aforesaid example of needle support assembly may also be associated with needles classified as 18G (total length needle 34 mm; length of needle projecting from the support 25 mm; outer diameter 1.2 mm and inner diameter 0.9 mm) and as 22G (total length needle 34 mm; length of needle projecting from the support 25 mm; outer diameter 0.70 mm and inner diameter 0.45 mm). In the case of the needle 22G the blood will fill the needle support assembly somewhat less (in any case at least the cone-shaped cavity 38 and one coil of both channels), in the case of a needle 18G the blood will fill the needle support assembly a little more with an improved visualisation.

The present invention also relates to a blood collection device 100 (as shown in particular in FIG. 2) comprising a needle support assembly 1 according to the invention (as described above) and an evacuated vial holder 101 connected to the needle support assembly 1.

The needle support assembly 1 according to the invention is provided with a vein needle V, partially inserted in the coupling seat 11, and a vial needle F, partially inserted in the coupling seat 12. The vial needle F is closed by a shut-off valve 24, preferably in perforable rubber, which encloses the projecting portion of the vial needle like a glove. The shut-off valve 24 is connected to the needle support assembly 1 at the free end of the tubular tail-piece 23. As illustrated for example in FIG. 4, the free end 25 of the tubular tail-piece 23 is shaped so as to define a coupling head for the valve 24.

The invention permits numerous advantages to be achieved, some of which already highlighted above.

The needle support assembly 1 according to the invention makes it possible to visualise in a clearer, more evident manner the correct entrance of the needle in the vein, thereby making it possible to easily recognise failure to enter the vein even in the case of a false indication related to a partial entrance of blood. The needle support assembly 1 therefore makes it possible to correctly verify the entrance of the needle in the vein.

The needle support assembly 1 according to the invention is operatively reliable. The operator may use it without risk of accidental effusions and in total safety.

The needle support assembly 1 according to the invention is in addition economically simple to produce.

The invention thus conceived thereby achieves the purposes set out.

Obviously, in its practical embodiments it may assume shapes and configurations different from those illustrated above while remaining within the present sphere of protection.

In addition, all the parts may be replaced by technically equivalent parts and the dimensions, forms and materials used may be chosen as needed.

The invention claimed is:

1. A needle support assembly for a venous blood collection device with evacuated vial, the assembly comprising:
   a support body that extends along a longitudinal axis between a first end and a second end at which a coupling seat for a vein needle and coupling seat for a vial needle are respectively made, said support body being provided with an inner chamber having an entrance and an exit which communicate fluidically with the vein needle coupling seat and with the vial needle coupling seat respectively to permit blood flow, said support body being made at least partially in transparent or semi-transparent material to permit visualisation of such blood flow,
   wherein, in relation to a section plane orthogonal to the longitudinal axis, the inner chamber has a mean cross-section greater than respective cross-sections of both the coupling seats and in that said inner chamber is divided into compartments communicating with each other which define at least two channels for the blood flow from the entrance to the exit,
   wherein said at least two channels are connected parallel to each other only next to the entrance and to the exit and being separate from each other, and
   wherein each of said at least two channels define a path for the blood that moves away from a straight line connecting the entrance and the exit and has a smaller cross-section than the mean cross-section of the inner chamber.

2. The needle support assembly according to claim 1, wherein the entrance and the exit are aligned longitudinally with each other and with the coupling seats, each channel defining a path for the blood which moves away from the longitudinal axis.

3. The needle support assembly according to claim 1, wherein said at least two channels mainly occupy an axially outermost portion of volume of the inner chamber.

4. The needle support assembly according to claim 1, wherein said at least two channels extend mainly on planes orthogonal to the longitudinal axis.

5. The needle support assembly according to claim 1, wherein said at least two channels each have a spiral-shaped extension.

6. The needle support assembly according to claim 5, wherein said at least two channels have a spiral extension around axes parallel to the longitudinal axis.

7. The needle support assembly according to claim 5, wherein said at least two channels extend in two axially superimposed spiral shaped paths, coaxial to the axis.

8. The needle support assembly according to claim 7, wherein a first channel of said at least two channels extends in a clockwise turning spiral and a second channel of said at least two channels extends in an anti-clockwise turning spiral.

9. The needle support assembly according to claim 1, wherein the support body comprises an outer containment casing, which defines the inner chamber, and a partitioning element which is positioned inside said casing to create said at least two one or more channels.

10. The needle support assembly according to claim 9, wherein said casing is composed of a socket body, provided on a bottom of the socket body with a first aperture which defines the entrance of the inner chamber and at which aperture the coupling seat for the vein needle is made.

11. The needle support assembly according to claim 10, wherein said partitioning element supports at one of its ends a flange which abuts with the socket body to close the inner chamber, a second aperture being made on said flange which defines the exit of the inner chamber and at which the coupling seat for the vial needle is made.

12. The needle support assembly according to claim 11, wherein the socket body of the casing is a cylindrical shape and wherein the partitioning element comprises an axially elongated body which extends from said flange coaxially to an axis of the cylindrical socket body, a plurality of tabs extending radially from such elongated body which divide the inner chamber into the aforesaid compartments.

13. The needle support assembly according to claim 12, wherein said tabs are in contact with the socket body of the casing.

14. The needle support assembly according to claim 12, wherein said tabs have a spiral shape extension around the axially elongated body.

15. The needle support assembly according to claim 14, wherein said tabs define between them two separate, axially superimposed spiral-shaped channels.

16. The needle support assembly according to claim 12, wherein said axially elongated body supports in an axially opposite position to the flange, a disc which has a cross-section corresponding to an inner transversal cross-section of the socket body, and which is placed next to the bottom of the socket body, on said disc one or more separate grooves being made, each of which places the first entrance aperture of the blood flow in communication with one of the aforesaid channels.

17. The needle support assembly according to claim 12, wherein at an axial portion next to the flange, said axially elongated body has an inner cavity which communicates fluidically with the second exit aperture of the inner chamber and with said at least two channels.

18. The needle support assembly according to claim 10, wherein the socket body of the outer casing is made in transparent or semi-transparent material at least for a first axial portion which extends from the bottom of the socket body.

19. A blood collection device, comprising a needle support assembly according to claim 1 and provided with a vein needle and a vial needle and an evacuated vial holder connected to said needle support assembly, wherein said vial needle, closed by a shut-off valve, projects inside the holder.

* * * * *